United States Patent [19]

Golden

[11] 4,108,146

[45] Aug. 22, 1978

[54] BENDABLE THERMAL PACK UNIT

[76] Inventor: Theodore Alan Golden, 1063 Ardmore, Birmingham, Mich. 48084

[21] Appl. No.: 797,029

[22] Filed: May 16, 1977

[51] Int. Cl.² ............................................. A61F 7/00
[52] U.S. Cl. ..................................... 128/400; 128/402
[58] Field of Search .............. 128/399, 400, 402, 82.1, 128/258

[56] References Cited

U.S. PATENT DOCUMENTS

| | | | |
|---|---|---|---|
| 500,568 | 7/1893 | Ells | 128/402 |
| 546,436 | 9/1895 | Springsteen | 128/402 |
| 1,777,982 | 10/1930 | Popp | 128/402 |
| 2,167,467 | 7/1939 | Sisson | 128/402 |
| 3,075,517 | 1/1963 | Morehead | 128/400 |
| 3,467,104 | 9/1969 | Burbridge et al. | 128/400 |
| 3,606,890 | 9/1971 | Gilbert | 128/400 |
| 3,683,902 | 8/1972 | Artemenko et al. | 128/82.1 |

Primary Examiner—Lawrence W. Trapp

Attorney, Agent, or Firm—Cullen, Settle, Sloman & Cantor

[57] ABSTRACT

A thermal pack unit or compress is formed by adhesively securing two relatively thin pieces together. The first piece is a plastic sheet having one or more interconnecting channels or grooves formed in a surface thereof to form a path for the circulation of the thermal fluid. The second piece is a relatively thin sheet of non-resilient bendable metal which is secured over the channeled surface of the plastic sheet for sealing the top portion thereof so the fluid inputted at one end of the channeled space is able to flow or circulate therethrough and then be outputted from an outlet in the channeled space. The metal sheet is bendable so that the pack unit can be readily conformed to a given contour of the human body such as the irregular areas about the eyes, nose and ears of a person and the characteristics of the metal insure that the contoured shape will be retained to aid in keeping the pack unit positioned while in use.

10 Claims, 8 Drawing Figures

U.S. Patent   Aug. 22, 1978   4,108,146
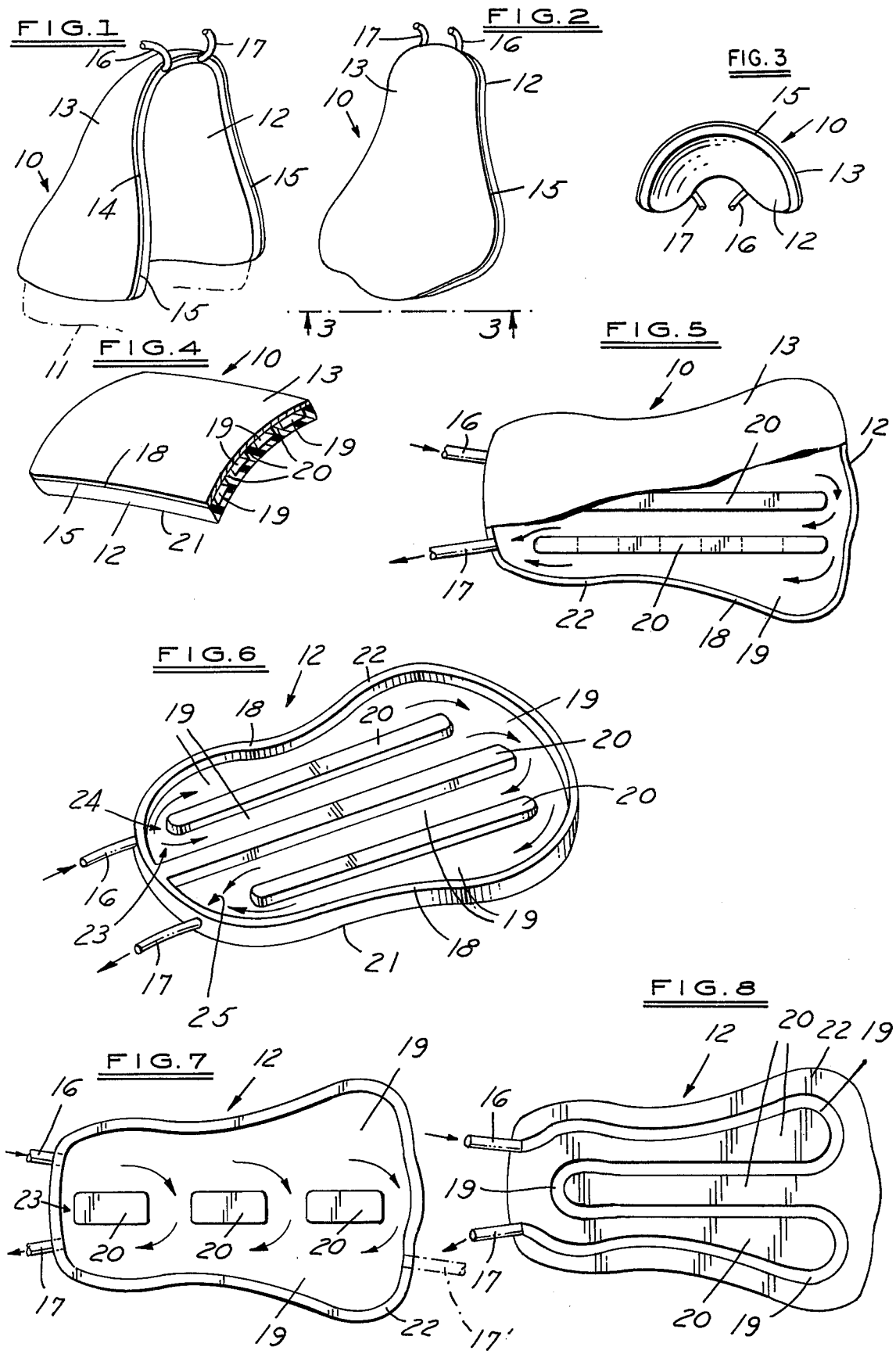

BENDABLE THERMAL PACK UNIT

BACKGROUND OF THE INVENTION

The present invention relates to thermal pack units or compresses for making hot or cold applications to various portions of the human body in medical treatment, and more particularly, to a therapeutic thermal pack unit which can be readily contoured to a predetermined portion of a person's body for maintaining a predetermined body temperature for therapeutic purposes.

A plurality of hot or cold applicators exist in the prior art whereby thermal fluid is circulated at a first temperature from a supply into an applicator and thence through a serpentine or convoluted path back out of the applicator to return the circulating fluid to the supply so that a continuous flow of fluid at the first temperature may be inputted to the applicator. Such systems are shown in U.S. Pat. Nos. 1,896,953; 2,726,658; and 3,683,902 which are incorporated by reference herein for teaching systems in which such applicator units may be used and for teaching thermal fluid storage and circulation means for such systems.

Such systems, however, suffer from many shortcomings. Nearly all such systems involve relatively thick and bulky compresses which do not conform closely to the contour of the human body such as those irregularly fromed areas about the eyes, nose and ears of a patient who has undergone plastic surgery or the like. Failure of the pack unit to conform closely about such areas and to retain close contact once positioned will result in one area being cooled at a first temperature while another adjacent area does not even contact the pack unit. This problem often results in irregular or non-uniform healing of the skin, swelling and the like.

One of the prime objects of the therapeutic pack unit or compress of the present invention is to enable it to be easily and closely conformed to any part of the human body which has recently undergone plastic surgery, a skin graft or the like, such as those areas of a human body about an eye, a nose, an ear, or the like, and then to insure that the relatively close contoured fit of the compress is maintained during the healing operation so as to prevent swelling and to retard the tendency of the newly-applied skin to die before the flow of blood begins.

The present invention eliminates the deficiencies of the prior art and provides a mechanically simple, low-cost, lightweight therapeutic pack unit or compress which can be readily molded to retainably conform closely to the contours of any portion of the human body and which will retain the conformed contour throughout the period of use without the need for constantly adjusting or recontouring the pack unit and without variations inposition due to variations in the pressure of the thermal fluid, thereby greatly enhancing the therapeutic value of the device of the present invention.

BRIEF SUMMARY OF THE INVENTION

The present invention provides a relatively thin bendable thermal pack unit adapted to be molded to conform closely to the contours of a portion of the human body and to retain the molded shape once it has been positioned to circulate a thermal fluid to heat or cool adjacent skin areas to aid in healing and the like.

The thermal pack unit of the present invention includes a bendable plastic web or sheet having at lease one channeled space formed in a surface thereof to form a path for the circulation of the thermal fluid therethrough. A relatively thin layer or sheet of non-resilient bendable material is secured over the channeled surface of the plastic web for sealing the top of the channeled space and defining a continuous fluid path through the pack unit. The material sheet is bendable to conform to a given contour and adapted to retain that contour to aid in keeping the thermal pack unit properly positioned upon any portion of the human body while in use. Means coupled to the ends of the channeled space are provided for circulating thermal fluid within the pack unit to heat or cool areas of the human body adjacent to the non-channeled surface of the plastic sheet.

The present invention provides a relatively simple, easy to make and easy to use pack unit which due to its relative thinness and to the non-resiliency of the metal sheet, can be molded to easily conform to any contour of the human body, such as those irregularly shaped areas about a person's eyes, nose, ears, or the like and which will retain its shape once contoured to aid the pack unit in staying in place throughout the period of use. The pack unit of the present invention is easily portable, disposable and able to selectively heat or cool any desired portion of the human body and it can be quickly and easily conformed to insure proper surface-to-surface contact and proper positioning once applied.

Other advantages and meritorius features of the present invention will be more fully understood from the following detailed description of the drawings and the preferred embodiment, the appended Claims and the drawings, which are briefly described hereinbelow.

BRIEF DESCRIPTION OF THE DRAWINGS

FIG. 1 is perspective side view of a contoured thermal pack unit of the present invention;

FIG. 2 is a perspective front fiew of the thermal pack unit of FIG. 1;

FIG. 3 is a bottom view of the thermal pack unit of FIG. 2 taken along view lines 3—3 thereof;

FIG. 4 is a sectional perspective view of the thermal pack unit of the present invention;

FIG. 5 is a top plan view, partially broken away, of the therapeutic bendable thermal pack unit of the preferred embodiment of the present invention;

FIG. 6 is a perspective view of the channeled plastic sheet portion of the bendable pack unit of the present invention showing the channeled portions thereof;

FIG. 7 is a top plan view of an alternate embodiment of the channeled plastic sheet of the present invention having different channeled configurations; and FIG. 8 is a top plan view of still another alternate embodiment of the channeled plastic sheet of the present invention wherein a single serpentine channel is employed.

DESCRIPTION OF THE PREFERRED EMBODIMENT

FIGS. 1, 2 and 3 illustrate the bendable thermal pack unit, compress or applicator 10 of the present invention as it would be molded to conform closely to a human nose 11. The bendable pack unit 10 is formed from two pieces. The first piece is a bendable plastic sheet or web 12 preferably made from a durable plastic material such as polyvinyl which can be easily and readily bent or formed to fit the contour of a predetermined portion of the human body.

Other materials, even a metal such as aluminum, can be used but soft plastic-like material is preferred for contact with human skin. The second piece is preferrably a relatively thin bendable metal sheet 13 which is secured over the channeled surface 14 of the plastic sheet 12 by means of an adhesive layer 15 or the like. The metal sheet 13 is made from some metal such as aluminum which is relatively non-resilient and which can be easily bent, formed or configured to fit the contour of a predetermined portion of the human body and which wll hold that contour for as long as desired so as to aid in keeping the thermal pack unit 10 positioned over the portion of the human body to which it has been contoured for the entire period of use without requiring frequent repositionings or readjustments. A plastic-type material could also be used so long as it is bendable and able to retain the contoured shape.

The thermal pack unit 10 of the present invention includes an input 16 such as a plastic or rubber tube which supplies thermal fluid from a source, such as a conventional circulation pump and cooler, to an input portion 24 of the channel of the plastic sheet 12, as hereinafter described. Similarly, the pack unit 10 includes an output 17 which may also be a hollow plastic or rubber tube which connects an output portion 25 of the channeled space of the plastic sheet 12 for returning the circulated thermal fluid to the source for reprocessing and possible recirculation, as conventionally known. The specific location of the input 16 and output 17 may be chosen to meet specific needs.

FIG. 4 is a section perspective view of the bendable thermal pack unit 10 of the present invention. The bendable plastic sheet 12 has a channeled interior surface 18 having one or more channel spaces or paths 19 formed therein. The channel spaces 19 may be separated by raised pedestal portions or separators 20 to form a network of interconnected channels or paths for circulating the thermal fluid. The non-channeled surface 21 is used to contact the body surface or skin portion of the human patient over which it is conformably applied. The plastic sheet 12 can, of course, be formed by any conventional means such as vacuum forming, molding using a lost wax technique or the like.

The relatively thin bendable sheet of metal 13 is retainably secured to the plastic sheet 12 such as by means of a layer of suitable adhesive or glue 15 so that the metal sheet 13 seals the upper surface of the channels 19 to prevent the escape of the thermal fluid therefrom so that the fluid will be received from a source of thermal fluid and inputted via inlet 16 into the channels 19 and then circulated therein before being outputted via the outlet 17 and returned to the source for further reprocessing as conventionally known.

FIG. 5 shows one embodiment of the present invention wherein various portions of the hollowed out channeled space 19 are partially separated from one another by means of the raised pedestal portions 20.

The pedestals 20 may be elongated formations as shown in FIG. 5 or they could be a series of individual formations as represented by the phantom lines in FIG. 5. A raised rim 22 is provided around the side of the plastic sheet 12 so that the top surface of the rim 22 and the top surface of the pedestal portions 20 can be used to apply the adhesive 15 which secures the metal sheet 13 over the channel spaces 19 to provide a fluid-tight seal thereover.

FIG. 6 shows a perspective view which better illustrates the interconnecting, hollowed-out channel spaces 19 and the raised pedestal portions 20 of the lower half or channeled plastic sheet 12 of the present invention. The thermal fluid is inputted into the header 23 at an input portion 24 of the hollow channel 19 via the fluid conduit or tube 16 and then circulated as shown by the arrows within the channel space 19 to be returned to an output header 25 and outputted therefrom via the outlet conduit or tube 17 to be returned to the source of thermal fluid for further reprocessing, as conventionally known. Of course, the output 17 could be provided at the opposite end and a single header 23 provided at the input end 24.

As previously indicated, the adhesive 15 would normally be applied to the upper surface of the outer rim or edge 22 of the sheet 12 and to the uppper surface of the pedestal portions 20. The upper surfaces of the pedestals 20 and the ridge portion 22 are coplanar so that by adhesively securing the sheet 13 thereto, the upper ends of the channels 19 are sealed so that the fluid is constrained to circulate within the channels 19 once it has been received via the input 16 and then outputted from the output conduit 17. FIG. 7 shows an alternate embodiment of the arrangement of the channel spaces 19 and pedestal portions 20 and any form, configuration and number of separate or interconnecting channels and pedestals may be used. The phantom lined outlet 17 illustrates an alternate outlet position. FIG. 8, for example, shows a single serpentine channel 19 used to circulate the thermal fluid within the channeled plastic sheet 12.

In the preferred embodiment of the present invention, the combination of the bendable channeled plastic sheet 12 with the relatively thin bendable non-resilient metal sheet 13 is such that the pack unit 10 can be easily configured to conform closely about any portion of the human body such as about those areas surrounding a person's eyes, nose, and ears and the pack unit 10 will retain that shape throughout the period of use to aid in keeping the pack unit 10 positioned to insure maximum effectiveness of the circulating fluid to facilitate healing and the like. The sides of the plastic sheet 12 and metal sheet 13 can also be configured or shaped, as shown in FIGS. 1, 2 and 8 to further aid in conforming the pack unit 10 about a particular body portion and the light weight and moldability of the pack unit will enable it to be quickly and easily applied and then retained in the applied position for long periods of time without the need for readjustments and the like.

The method of making the bendable therapeutic thermal pack unit 10 of the present invention contemplates the step of forming a first sheet of bendable plastic material with one or more channels and then providing the sheet with input means at one end of the channel and output means at another portion of the channel. A sheet of bendable yet non-resilient metal is then sealably secured over the channeled surface of the plastic sheet to seal the top of the channels and the unit is ready for use.

With this detailed description of the specific apparatus used to illustrate the preferred embodiment of the present invention and the operation thereof and the method of making same, it will be obvious to those skilled in the art that various modifications can be made in the bendable therapeutic thermal pack unit of the present invention and in the materials and specific configurations used therein without departing from the spirit and scope of the present invention which is limited only by the appended claims.

I claim:

1. A relatively thin bendable thermal pack unit adapted to be molded to conform closely to the contours of a portion of a human body and to retain the molded shape when positioned to circulate a thermal fluid to heat or cool adjacent skin areas to aid in healing and the like, said thermal pack unit comprising a bendable plastic-like web having at least one channeled space formed in a surface thereof to form a fluid path for the circulation of a thermal fluid, a relatively thin sheet of non-resilient bendable material secured over said channeled surface of said plastic-like web for sealing the top of said channeled space, said relatively thin sheet being bendable to conform to a given contour and adapted to retain that contour to aid in keeping the positioned thermal pack unit in place upon a portion of a human body, and means coupled to outlets in the channeled space for circulating thermal fluid therein to heat or cool areas of the human body adjacent the non-channeled surface of said plastic-like web.

2. The bendable thermal pack unit of claim 1 wherein said relatively thin sheet of non-resilient bendable material includes a dead metal which is easily bent and which retains the shape of the bend even after the bending force is removed therefrom.

3. The bendable thermal pack unit of claim 2 wherein said thin sheet of non-resilient bendable metal includes aluminum.

4. The bendable thermal pack unit of claim 1 includes inlet means at one end of the plastic-like web for communicating with an input portion of the channeled space formed therein for receiving said thermal fluid for circulation within said channeled space and an output at another portion of said channeled plastic-like web for receiving the circulated thermal fluid after it has been circulated within said pack unit.

5. The bendable thermal pack unit of claim 1 wherein said at least one channeled space includes a plurality of parallel channels separated by pedestal portions integral with the floor of the plastic web for providing circulation paths within said channeled space.

6. The bendable thermal pack unit of claim 1 wherein said at least one channeled space includes a continuous serpentine channel having an input and an output coupled to said means for circulating thermal fluid within said pack unit.

7. The bendable thermal pack unit of claim 1 wherein said bendable plastic-like web includes a plurality of spaced pedestal portions integral with a portion thereof for dividing said at least one channeled space into a plurality of paths for circulating said thermal fluid therethrough.

8. The bendable thermal pack unit of claim 1 further including adhesive means for sealably securing said relatively thin sheet of non-resilient bendable material over the channeled surface of said plastic-like web to prevent the escape of said thermal fluid from said channeled space.

9. The bendable thermal pack unit of claim 1 wherein said thermal fluid is maintained at a termperature lower than the temperature of a human body for enabling said pack unit to be used in an area having recently undergone plastic surgery, skin graft and the like to reduce the tendency of the skin cells to die while giving time for the new blood cells to take over and aid in the healing process.

10. The bendable thermal pack unit of claim 1 wherein said bendable plastic-like web includes a highly durable, relatively soft, bendable plastic material such as cast polyvinyl.

* * * * *